United States Patent [19]

Gibson

[11] Patent Number: 4,606,332

[45] Date of Patent: Aug. 19, 1986

[54] BACK TREATMENT APPARATUS

[76] Inventor: Howard W. Gibson, Star Rte., Tribune, Kans. 67879

[21] Appl. No.: 649,220

[22] Filed: Sep. 10, 1984

[51] Int. Cl.[4] .................... A61F 5/00

[52] U.S. Cl. .................... 128/71; 128/70

[58] Field of Search .................... 128/70, 71, 72, 73, 128/74

[56] References Cited

U.S. PATENT DOCUMENTS

| | | | |
|---|---|---|---|
| 1,071,621 | 8/1913 | Loranger | 128/72 |
| 1,171,713 | 2/1916 | Gilkerson | 128/72 |
| 1,301,071 | 4/1919 | Marshall | 128/73 |
| 1,427,004 | 8/1922 | McManis | 128/73 |
| 1,582,950 | 5/1926 | Weaver | 128/72 |
| 2,002,349 | 5/1935 | Lundeen | 128/72 |
| 2,217,783 | 10/1940 | Bell | 128/73 |
| 2,475,003 | 7/1949 | Black | 128/71 |
| 2,622,950 | 12/1952 | Nimmo | 128/73 |
| 3,302,641 | 2/1967 | Berne | 128/71 |
| 3,998,218 | 12/1976 | Lane | 128/70 |
| 4,503,844 | 3/1985 | Siczek | 128/71 |

FOREIGN PATENT DOCUMENTS

| | | | |
|---|---|---|---|
| 171985 | 7/1960 | Sweden | 269/324 |

*Primary Examiner*—Edgar S. Burr
*Assistant Examiner*—Tonya Eckstine
*Attorney, Agent, or Firm*—Phillip A. Rein

[57] ABSTRACT

This invention is a back treatment apparatus having fully adjustable features for supporting a person's body to be stretched there across for treatment of various body problems. The back treatment apparatus includes a main housing; a foot support connected to the main housing 14 and adjustable relative thereto; an adjustable body support mounted within the main housing; and a control means operable to move portions of the main housing, foot support, and the adjustable support. The housing is formed in two sections so that one section can be moved relative to the other through the control. The foot support can be adjustable vertically and laterally as required. The adjustable body support includes a forward body support assembly; a middle body support assembly; and a rear body support assembly. All of the support assemblies above-mentioned can be adjustable so as to achieve a desired contour for exercising and stretching of the person's body utilizing same. The control means provides finger tip available actuator switches operable to readily adjust the main housing; foot support; and the numerous areas of the adjustable body supports.

7 Claims, 6 Drawing Figures

BACK TREATMENT APPARATUS

PRIOR ART

A patentability investigation was conducted on the above-identified invention and the following U.S. patents are noted:

U.S. Pat. No. 3,489,142
U.S. Pat. No. 3,042,025
U.S. Pat. No. 3,747,916
U.S. Pat. No. 3,821,953
U.S. Pat. No. 4,157,089
U.S. Pat. No. 4,354,485

The Benson patent discloses a chiropractic table having a central humped portion and an opening for patients to place their heads therethrough or rest the same thereon. The table is provided with an arm rest but is not operable in a manner similar to our invention claimed herein.

The Loughrey patent discloses a table for treatment of people that need to have their lungs drained and is merely a table being fully adjustable to place people in proper angular relationships. The Safadago patent discloses a prone board having several adjustable features but the main portions for supporting the hips, legs, and back are lying in a common plane and, therefore not operable in a matter similar to our invention setforth herein.

The Golay and Mikan patents disclose adjustable structures to raise and lower the portion of the body to permit the force of gravity to act thereon.

The Jackson patent discloses a structure having a force of gravity acting upon one's body and having a central vibrator structure. The Jackson device can only be adjusted in a limited fashion.

PREFERRED EMBODIMENT OF THE INVENTION

In one preferred embodiment of this invention, a back treatment apparatus is provided including (1) a main housing means; (2) a foot support means movably connected to the main housing means; (3) an adjustable body support means mounted upon the main housing means; and (4) a control means operable to control movement of the foot support means and the adjustable body support means. The main housing means includes a first body support housing and a second body support housing which is movable relative to the first body support housing and adapted to support a portion of a person's body thereon. The foot support means includes a movable support frame assembly having a foot covering assembly thereon and operable to receive a portion of a person's foot thereon for support. The adjustable body support means includes (1) a forward body support assembly; (2) a middle body support assembly; and (3) a rear body support assembly. The noted body support assemblies are physically mounted to the main housing means and easily adjustable as desired so as to fit the needs of a person utilizing this invention. The control means includes an actuator panel assembly having numerous actuator switch members which each are independently operable in order to (1) to separate the first body support housing and the second body support housing if so desired; (2) move the foot support means inwardly and outwardly relative to the main housing needs; (3) adjust the forward body support assembly; (4) adjust the middle body support assembly; and (5) adjust the rear body support assembly. The back treatment apparatus of this invention is fully adjustable so as to place and support a person's body thereon in a precise position to achieve the treatment that is required.

OBJECTS OF THIS INVENTION

One object of this invention is to provide a back treatment apparatus being of an inverted "4" shape so as to drape a person's body thereover as the main purpose of the invention is the treating of back ailment problems.

Still, one other object of this invention is to provide a back treatment apparatus adapted to support a person's body thereon in a prone position having numerous adjustable features so as to support the person's body thereon in the most advantageous condition for treatment.

Still, another object of this invention is to provide a back treatment apparatus having a main housing means which is made in half sections and adjustable relative thereto to compensate for the height of a person utilizing the same.

One further object of this invention is to provide a back treatment apparatus having numerous adjustable body support means thereon which are readily adjustable through a control means using electric motors or hydraulic motors for precise adjustment.

One other object of this invention is to provide a back treatment apparatus which is sturdy in construction, attractive in appearance, having numerous adjustable features thereon; substantially maintenance free; and easy to use.

Various other objects, advantages, and features of the invention will become apparent to those skilled in the art from the following discussion, taken in conjunction with the accompanying drawings, in which:

FIGURES OF THE INVENTION

Figures 1, 2:
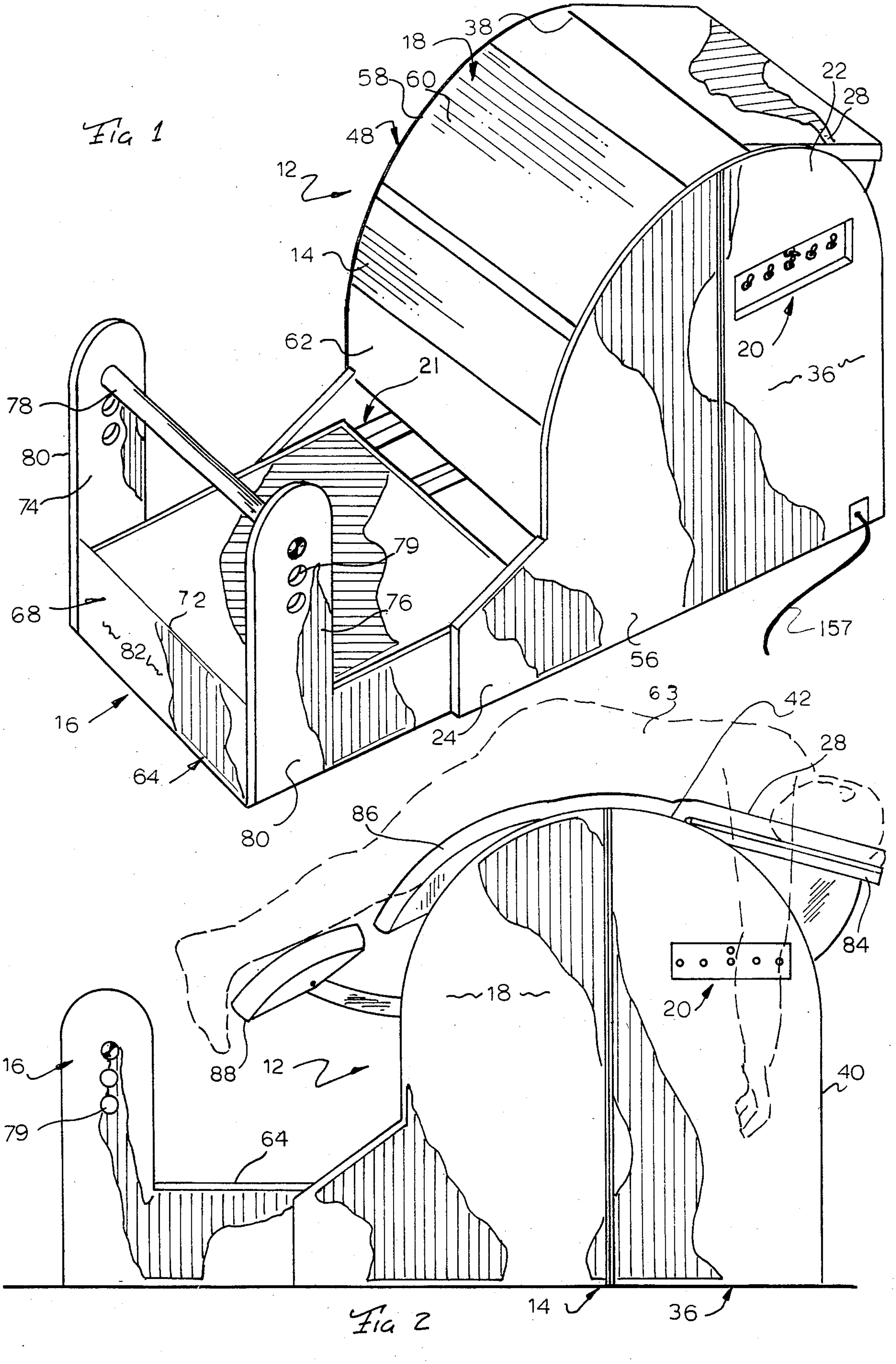
FIG. 1 is a perspective view of the back treatment apparatus of this invention.
FIG. 2 is a side elevational view of the back treatment apparatus of this invention illustrating the outline of a person utilizing the same.

The following is a discussion and description of preferred specific embodiments of the new back treatment apparatus of this invention, such being made with reference to the drawings, whereupon the same reference numerals are used to indicate the same or similar parts and/or structure. It is to be understood that such discussion and description is not to unduly limit the scope of the invention.

DESCRIPTION OF THE INVENTION

Referring to the drawings in detail and, in particular to FIG. 1, the back treatment apparatus of this invention, indicated generally at 12, includes (1) a main housing means 14; (2) a foot support means 16 adjustably connected to the main housing means 14; (3) an adjustable body support means 18 connected to the main housing means 14; (4) a control means 20 mounted on said main housing means 14 and operable to arcuate the adjustable body support means 18 and the foot support means 16 as will be explained; and (5) a housing and foot separator means 21 to move the main housing means 14 and the foot support means 16.

The main housing means 14 includes a first body support housing 22 having a movable second body support housing 24 connected thereto. The first body support housing 22 includes a first support frame assembly 26 having a first outer covering assembly 28 mounted thereon.

Figure 3:
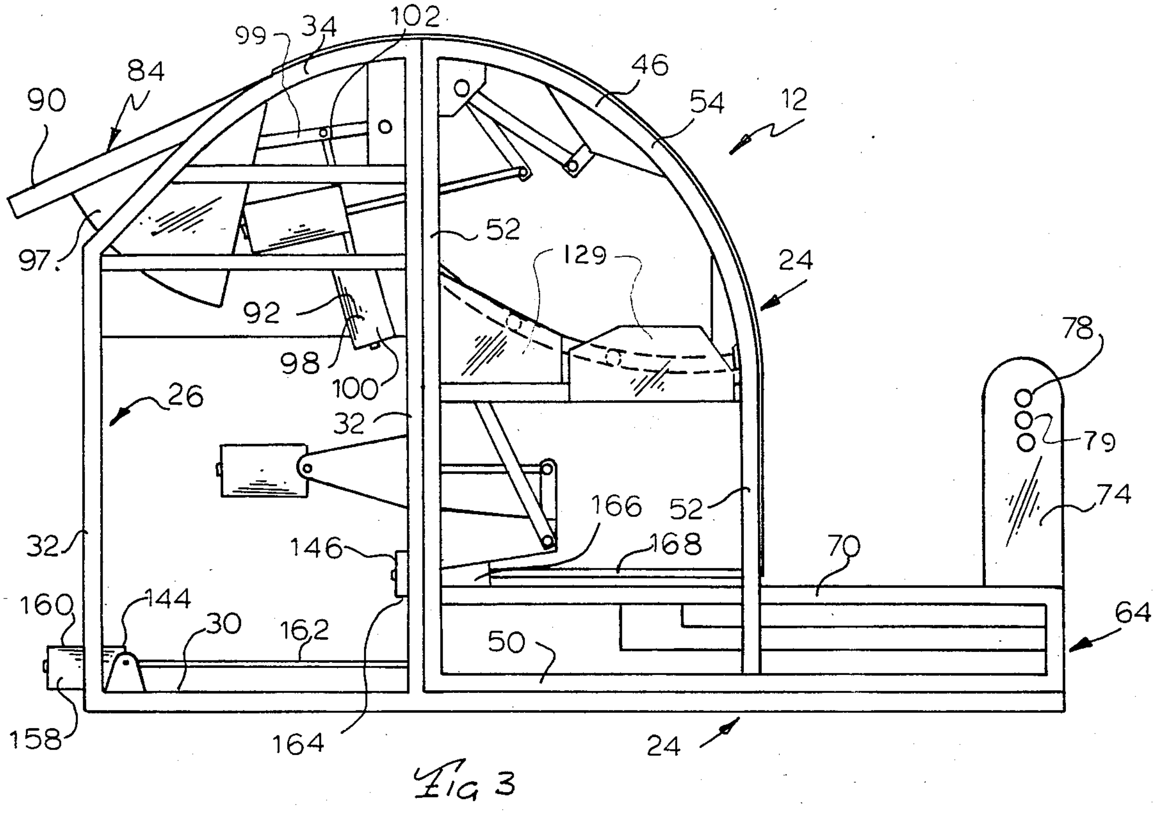
FIG. 3 is a side elevational view of the back treatment apparatus of this invention in the substantially folded or nonexpanded conditions.

As best shown in FIG. 3, a side view of the first support frame assembly 26 which is substantially identical on the opposite side thereof and interconnected by support struts. The first support frame assembly 26 includes (1) a bottom support frame 30; (2) side vertical support members 32 connected to the bottom support frame 30; and (3) an arcuate shape top support member 34 connected to the side support members 32. It is obvious that transverse support or strut members 35 interconnects the first support frame assembly 26 to the similar structure on the opposite side thereof to provide a main support frame.

As best shown in FIG. 1, the first outer covering assembly 28 includes (1) side cover members 36 and 38; (2) a front cover member 40; (3) a top cover member 42; and (4) an intermediate cover member 44. It is obvious that the first outer cover assembly 28 may be of a vinyl or paneling material of such to receive a person's body thereon and be attractive in appearance.

Figure 4:
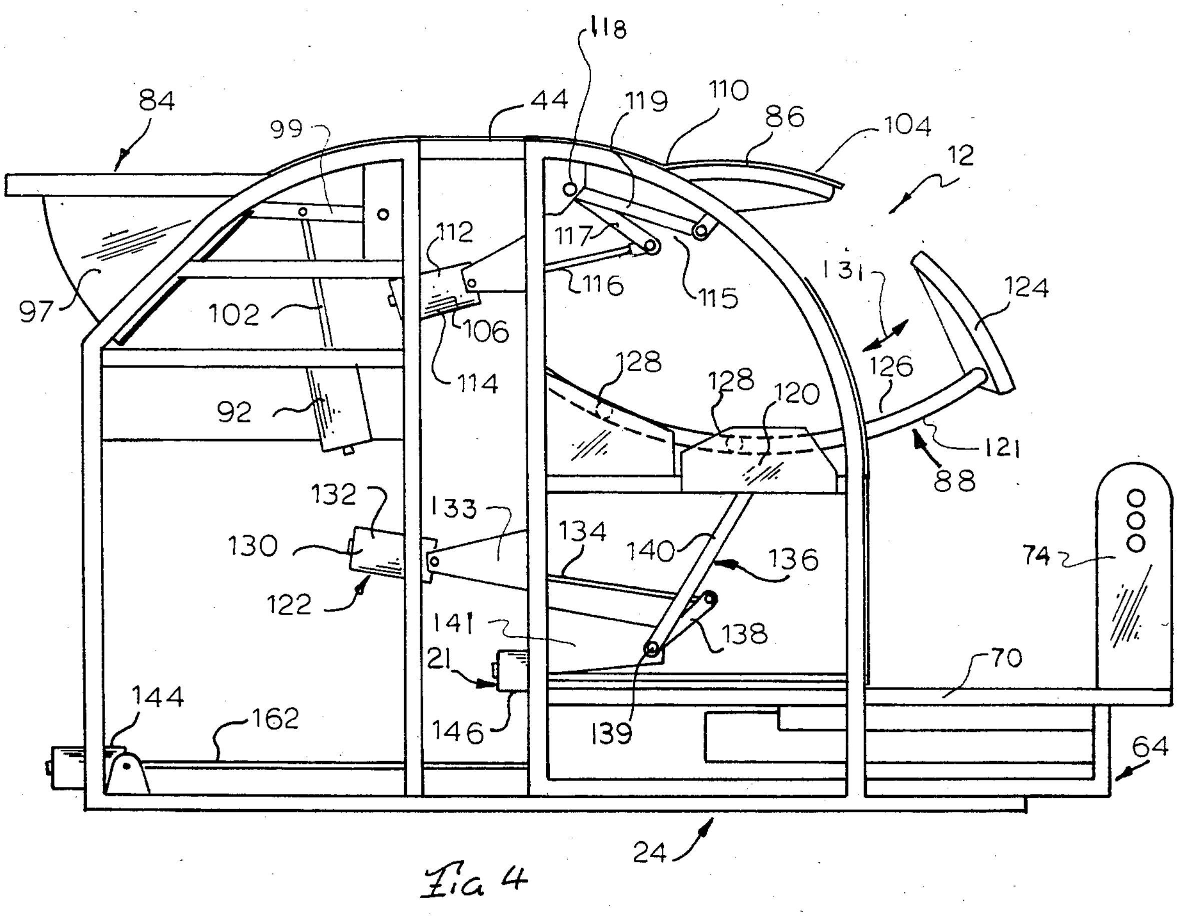
FIG. 4 is a side elevantional view similar to FIG. 3 illustrating the back treatment apparatus of this invention in the fully expanded condition.
Figure 5:
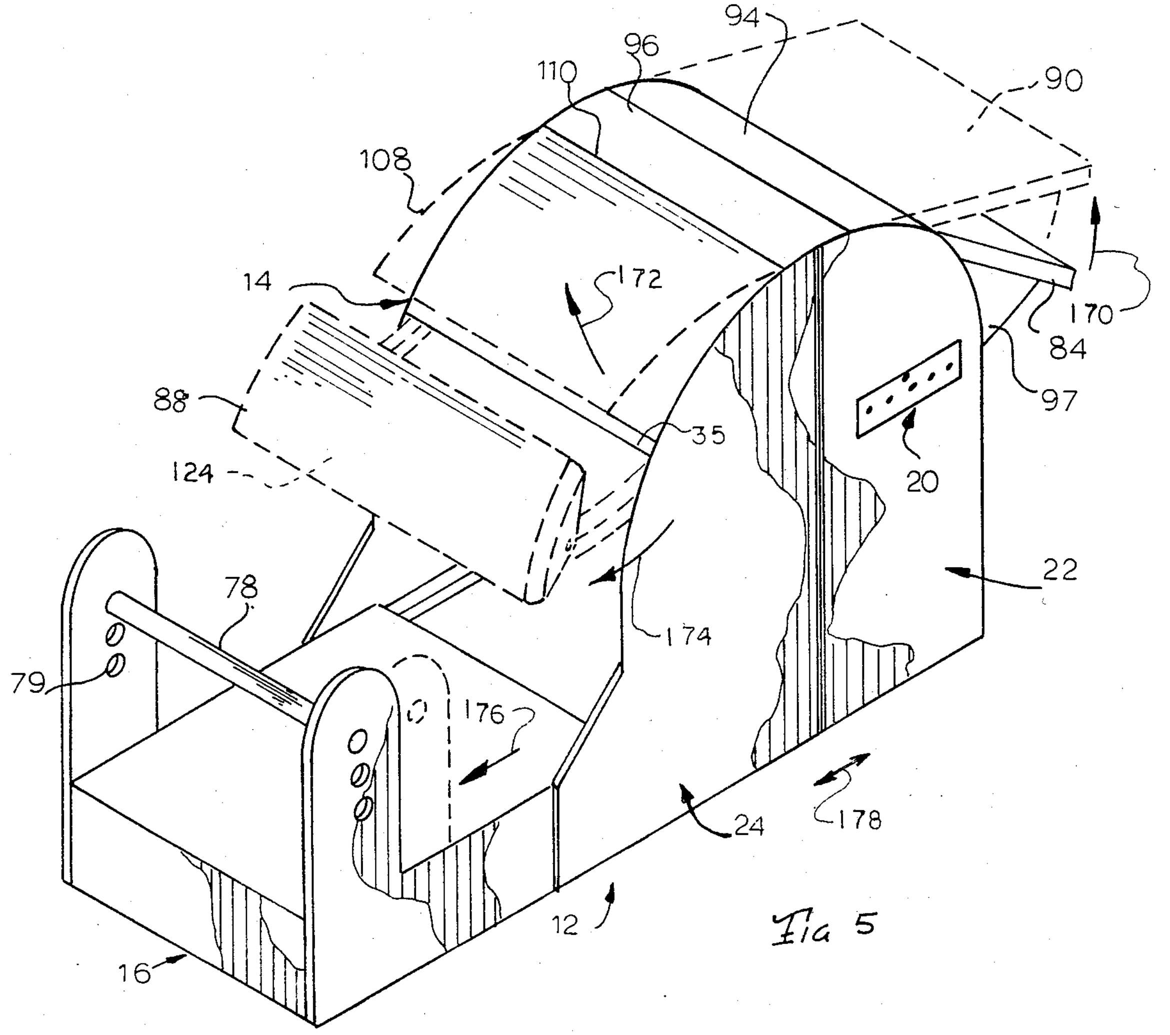
FIG. 5 is a perspective view of the back treatment apparatus of this invention again the expanded movement of its elements in dotted lines.

The intermediate cover member 44 is similar to a leaf on an expandable dinner table which is operable to cover the opening between the first body support housing 22 and the second body support housing 24 when in the expanded condition is noted in FIG. 4.

The second body support housing 24 includes a second support frame assembly 46 having a second outer covering assembly 48 mounted thereon. The second support frame assembly 46 includes (1) a bottom support frame 50; (2) a vertical side support member 52 connected to the bottom support frame 50; and (3) an arcuate top support member 54. Is obvious that the second support frame assembly 46 as shown in FIG. 3 is duplicated on the opposite side thereof and interconnected by the transverse support or strut members 35 so as to provide a main support frame.

The second outer covering assembly 48 is merely to provide a decorative and support surface for the person's body thereon and includes (1) side cover members 56 and 58; (2) a front cover member 60; and (3) a back cover member of 62. As stated for the first outer covering assembly 28, the second outer cover assembly 48 can be constructed of a vinly or panel material which can be padded if so desired and adapted to receive a person's body 63 draped thereon as illustrated in FIG. 2.

The foot support means 16 includes a movable support frame assembly 64 having a foot covering assembly 68 mounted thereon. The movable support frame assembly 64 includes (1) a pair of side support frames 70; (2) transverse support members 72 connected to the spaced side support frames 70; (3) L-shaped foot support members 74 and 76 secured to the side support frames 70; and (4) a foot support bar 78 mounted in adjustment holes 79 in the foot support members 74 and 76. It is obvious that the foot support bar 78 may be adjustably mounted in selective ones of the axially aligned adjustment holes 79 in a manner to be explained.

The foot cover assembly 68 is provided with foot side cover members 80 and a foot rear cover member 82 of vinyl or paneling material to provide a decorative outer appearance thereto to match the cover assemblies as previously described.

The adjustable body support means 18 includes (1) a forward body support assembly 84; (2) a middle body support assembly 86; and (3) a rear body support assembly 88. The forward body support 84 includes a movable forward support member 90 which is movable through the use interconnected actuator assembly 92.

The movable forward support member 90 includes a main support member 94 which is physically connected to the main housing means 14 through the use of a hinge member 96. The main support member 94 is given additional support through sides support members 97 which also protects and keeps a person utilizing same from getting his arms or other portions of his body caught under the main support member 94 when raising and lowering the same through the actuator assembly 92.

The actuator assembly 92 includes a screw motor member 98 or piston and cylinder assembly 100 which is operable to axially move a connector shaft 102. The motor member 98 or piston and cylinder assembly 100 is physically connected to the first support frame assembly 26 best shown in FIGS. 2, 3, and 4. It is obvious that the connector shaft 102 which has its outer end physically connected through a linkage member 99 connected to the main support member 94 and operable on rotation thereof to raise and lower the forward support member 90 about the hinge member 96.

The middle body support assembly 86 includes a movable middle support member 104 which is actuated through a middle actuator assembly 106. The movable middle support member 104 includes a middle support body member 108 which is pivotally connected through a hinge member 110 to the second support frame assembly 46 for movement thereof is shown in FIGS. 3 and 4.

The middle actuator assembly 106 includes a screw motor member 112 or a piston and cylinder assembly 114 which is pivotally connected to the second support frame assembly 46 for operation thereof in a manner to be explained.

The middle actuator assembly 106 further includes a connector shaft axially movable by the motor member 112 or the piston and cylinder assembly 114 and having an outer end of the connector shaft 116 connected to a linkage assembly 115. The linkage assembly 115 includes a first link member 117 pivotally connected at one end to the connector shaft 116 and connected at 118 to a second link member 119. The first link member 117 and the second link member 119 move as a unit about the point 118. The middle support body member 108 is movable about the hinge member 110 from the closed condition as shown in FIG. 3 to the fully expanded position shown in FIG. 4.

The rear body support assembly 88 includes (1) a movable rear support member 121; (2) an arcuate support rail assembly 120 connected to the second support frame 46 and adapted to receive the movable rear support member 121 thereon; and (3) a rear actuator assembly 122 having a portion thereon physically connected to the second support frame assembly 46.

The movable rear support member 121 includes a main rear support body member 124 adapted to contact a thigh or leg portion of a person utilizing this invention.

The actuate support rail assembly 120 include a pair of spaced rail members 126 each having an outer end thereof connected to the rear support body 124 and a central portion connected to roller members 128 which are movable within roller support members 129.

The co-action of the rail members 126 connected to the roller members 128 which are movable within the roller support members 129 allows for the arcuate movement of the rear support body member 124 as shown by an arrow 131 in FIG. 4.

The rear actuator assembly 122 includes (1) a screw motor member 130 or a piston and cylinder assembly 132 which is pivotally connected to the second support frame assembly 46 by a plate 133; (2) a connector shaft 134 which is axially movable by either the motor member 130 or the piston and cylinder assembly 132; and (3) a linkage assembly 136 which is movable by the connector shaft 134.

The linkage assembly 136 includes a first link member 138 rigidly connected at point 139 to a second link member 140. One end of the first link member 138 is pivotally connected to the connector shaft 134 and the other end at point 139 pivotally mounted in a support plate 141 in the second support frame 46. The second link member 140 which is connected at one end to the first link member 138 at the point 139 and an outer end is pivotally connected to the rail members 136. The outer end of the second link member 140 is pivotally connected to the rail member 126 to achieve the outward and upward arcuate movement indicated by the arrow 131 from the closed condition of FIG. 3 to the fully extened condition fo FIG. 4 and any desirable spaced increment therebetween.

The control means 20 includes an actuator panel assembly 142 having actuator switch members which are operable through a conventional electrical power supply to actuate the respective of aforemention screw motor members or piston and cylinder assemblies to operate same in a conventional manner. The screw motor members are of a dual direction type so as to be rotated in the needed direction to move the threaded connector shafts connected thereto to achieve operation of the adjustable body support means 18 of this invention. Also, the control means 20 may consist of hydraulic actuator levers which would be operable to direct fluid to opposite ends of the piston and cylinder assemblies described herein so as to move the connector shafts inwardly and outwardly. It is obvious that the use of screw motor members or piston and cylinder assemblies would achieve the same operation of movement of the adjustable body support means 18 as will be described.

Figure 6:
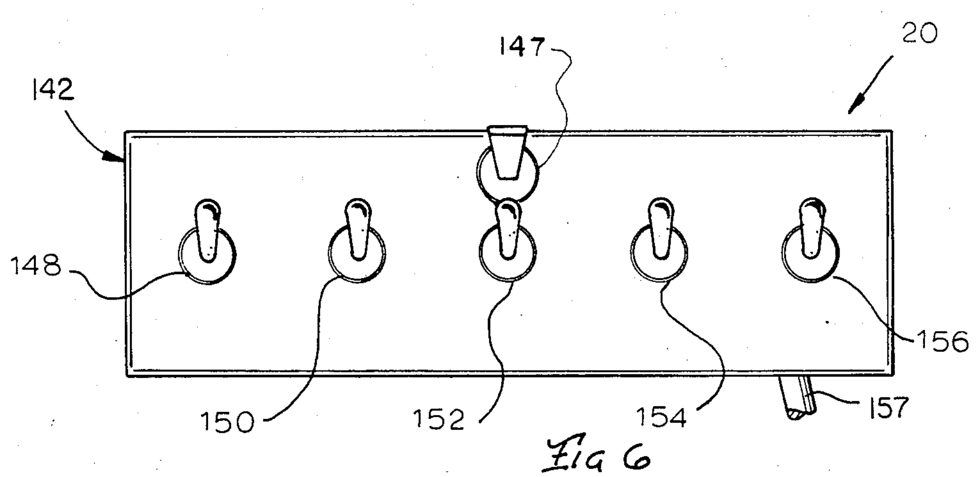
FIG. 6 is an enlarged fragmentary side elevational view of a control means of this invention.

As shown in FIG. 6, the actuator panel assembly 142 includes (1) a power on-off actuator switch 147; (2) a housing actuator switch 148; (3) a forward actuator switch 150; (4) a middle actuator switch 152; (5) a rear actuator switch 154; (6) a foot actuator switch 156; and (7) an electrical power supply card 157. The housing actuator switch 148 is operable to move the second body support housing 24 relative to a stationary first body support housing 22 from the closed condition of FIG. 3 to the fully opened condition of FIG. 4 or to any desirable spaced increment therebetween.

The forward actuator switch 150 is operable to move the forward body support assembly 84 or, more particularly, the forward support body 90 from the inclined position shown in FIG. 3 to the fully extended position of FIG. 4 or to any desired increment position therebetween.

The middle actuator switch 152 is operable to pivot the movable middle support member 104 from the closed condition as shown in FIG. 3 to the fully open position of FIG. 4 or any desired increment position therebetween.

The rear actuator switch 154 is operable to move the movable rear support body member 124 in an arcuate movement thereof from the closed condition as shown in FIG. 3 to the fully extended position as shown in FIG. 4 or any desired increment position therebetween.

The foot actuator switch 156 is operable to move the foot support means 16 from the closed position as shown in FIG. 3 to the fully open position as shown in FIG. 4 or any desired increment position therebetween.

The housing and foot separator means 21 includes (1) a housing separator assembly 144; and (2) a foot housing separator assembly 146. The housing separator assembly 144 includes (1) a screw motor member 158 or piston and cylinder assembly 160 which is pivotally connected to the first support frame assembly 26; and (2) a connector shaft 162 connected to the screw motor member 158 or the piston and cylinder assembly 160. The connector shaft 162 is movable axially by having an outer end connected to the second body support housing 24 or the second support frame assembly 46 for moving same from the closed position as shown in FIG. 3 to the fully extended position as shown in FIG. 4 or to any desired adjusted increment position therebetween.

The foot housing separator assembly 146 includes (1) a screw motor member 164 or piston and cylinder assembly 166 pivotally mounted on the second support frame assembly 46; and (2) the motor member 164 or piston and cylinder assembly 166 is connected to a connector shaft 168. The connector shaft 168 is movable axially be either the screw motor member 164 or the piston and cylinder assembly 166 to move the foot support means 16 from the closed position as shown in FIG. 3 to fully the extended position as shown in FIG. 4 or any desired increment position therebetween.

USE AND OPERATION OF THE INVENTION

The back treatment apparatus 12 of this invention is to be utilized for stretching and exercise of the muscles and/or ligaments and treating of the spinal column of the person 63 using same. The back treatment aparatus 12 is generally utilized in the manner as shown in FIG. 2 whereupon the person's body 63 is laid there across for stretching purposes. This type of treatment has been proven to be very successful by the inventor herein by treatment of his own back and spinal cord ailments with great success. It is noted that a person utilizing the back treatment apparatus 12 can first use the foot support means 16 for mounting himself upon and over the main housing means 14 as shown in FIG. 2.

Next, the forward body support assembly 84 can be adjustable by movement as shown by the arrow 170 to provide the desired stretching of the shoulder and neck muscles as required. Also, the forward body support assembly 84 is adjustable by the forward actuator switch 150 to achieve a comfortable position for one utilizing the same.

Next, the middle body support assembly 86 can be adjusted as shown by the arrow 172 to provide for the desired stretching of the spinal column and back muscles depending on the ailment of the person utilizes the same considering the body size, and shape. The middle body support assembly 86 can be adjusted as desired by operation of the middle actuator switch 152.

The rear body support assembly 88 is operated to move the rear body support member 124 to a desired position as shown by the arrow 174. The rear body support member 124 can be adjusted as desired by operation of the rear actuator switch 154.

The second body support housing 24 can be moved relative to the first body support housing 22 as desired through the control means 20 as shown by an arrow 178. The second body support housing 24 can be adjusted as desired by operation of the housing actuator switch 148. The intermediate cover member 44 may be utilized to cover an open area between the first body support housing 22 and the second body support housing 24.

Next, the foot housing separator assembly 146 can be actuated by the foot actuator switch 156 so as to move the foot support means 16 inwardly and outwardly as shown by the arrow 176 if the person desires to rest the arch of his foot thereon depending on the necessary treatment desired.

It is seen that the control means 20 through the actuator panel assembly 142 is readily available to the person's right hand utilizing the back treatment apparatus 12 as shown in FIG. 2 so that all the aforementioned adjustable features can be readily controlled so that the desired stretching and treatment of the person's body is achieved.

It is seen that the back treatment apparatus provides a main housing means which is sturdy in construction, easily adjustable, and attractive in appearance. The foot support means can be readily adjustable both in spacing from the main housing means and also in the height of a foot support member. The adjustable body support means provides three different features for adjusting supporting structure for (1) the head and shoulder portions of the person utilizing the same; (2) the central or midportion of the person's body and; (3) the leg or calf portion of the person utilizing the invention. Also, the main housing means is operable to be expanded in width to accommodate short and tall body frames.

It is seen that the back treatment apparatus is sturdy in construction, simple to use, having multiple adjustment features; and requiring a minimum amount of maintenance.

While the invention had been described in conjunction with preferred specific embodiments thereof, it is to be understood that this description is tended to illustrate and not to limit the scope of the invention, which is defined by the following claims.

I claim:

1. A back treatment apparatus adapted to receive a person's body thereon for treatment of medical back problems or the like, comprising:

(a) a main housing means;

(b) an adjustable body support means mounted on said main housing means including (1) a forward body support assembly pivotally connected to said main housing means; (2) a middle body support assembly pivotally connected to a midportion of said main housing means; and (3) a rear body support assembly movably connected to a rear portion of said main housing;

(c) said forward body support assembly, said middle body support assembly, and said rear body support assembly in one adjusted extreme closed condition forms a continuous support surface for a person's head, chest, mid-body portion, and lower body portion in a generally semicircular shape; and (d) a control means operably connected to said adjustable body support means to independently and automatically (1) move said forward body support assembly in a vertical inclined arcuate path; (2) move a portion of said middle body support assembly in a vertical inclined, arcuate path; and (3) move a portion of said rear body support assembly in a rearwardly inclined arcuate path;

(e) said main housing means includes a first body support housing and a second body support housing movably mounted on said first body support housing; and (f) said first body support housing and said second body support housing having an upper body support surface between said forward body support assembly and said middle body support assembly; and (g) a housing separator assembly connected between said first body support housing and said second support housing and operably connected to said control means for selective movement of said second body support housing laterally of said first body support housing.

2. A back treatment apparatus as described in claim 1, wherein:

(a) said forward body support assembly includes a movable forward support member having an actuator assembly connected thereto;

(b) said movable forward support member includes a main support member pivotally connected along a horizonally extended edge to said main housing means to support a person's upper body portion thereon in a selectively adjustable position; and (c) said main support member pivotally movable in increments from said adjusted closed condition to the generally horizontal said adjusted open condition.

3. A back treatment apparatus as described in claim 1, wherein:

(a) said middle body support assembly includes a movable middle support member having a middle actuator assembly connected thereto;

(b) said middle body support assembly includes a middle support member pivotally connected along a horizontally extended edge to said main housing means to support a person's mid body portion in a selectively adjustable position; and (c) said middle support member pivotally movable in increments from said adjusted closed condition to the generally horizontal said adjusted open condition.

4. A back treatment apparatus as described in claim 1, wherein:

(a) said rear body support assembly includes a movable rear support member having a rear actuator assembly connected thereto; and (b) said rear support member includes a rear support body member connected to said main housing means and movable in an arc to move said rear support body member conjointly outwardly and upwardly and being operable to support a lower portion of a person's body thereon in a selectively adjustable position.

5. A back treatment apparatus as described in claim 1, wherein:

(a) said forward body support assembly includes a movable forward support member having an actuator assembly connected thereto;

(b) said movable forward support member includes a main support member pivotally connected to said main housing means to support a person's upper body portion thereon in a selectively adjustable position;

(c) said middle body support assembly includes a movable middle support member having a middle support member having a middle actuator assembly connected thereto;

(d) said middle body support assembly includes a middle support member pivotally connected to said main housing means to support a person's mid body portion in a selectively adjustable position;

(e) said rear body support assembly includes a movable rear support member having a rear actuator assembly connected thereto;

(f) said rear support member includes a rear support body member connected to said main housing means and movable in an arc being operable to support a lower portion of a person's body thereon in a selectively adjustable position;

(g) a foot support means movably connected to said main housing means;

(h) said foot support means includes a foot support bar operable to be adjusted vertically; and (i) said control means includes a foot actuator switch operable to selectively move said foot support means laterally and horizontally relative to said main housing means.

6. A back treatment apparatus as described in claim 1, wherein:

(a) said forward body support assembly and said middle body support assembly in one adjusted open condition forms a continuous support surface for a person's head, chest, and mid-body portion in a generally horizontal plane.

7. A back treatment apparatus as described in claim 6, wherein:

(a) said rear body support assembly in an adjusted open condition cooperates with said middle body support assembly to support a person's thigh and leg portions in a common inclined plane.

* * * * *